US011306281B2

(12) United States Patent
Saito

(10) Patent No.: US 11,306,281 B2
(45) Date of Patent: Apr. 19, 2022

(54) CULTURE DEVICE, CULTURE METHOD AND CULTURED ORGAN PRODUCED BY THE CULTURE METHOD

(71) Applicant: Koji Saito, Tokyo (JP)

(72) Inventor: Koji Saito, Tokyo (JP)

( * ) Notice: Subject to any disclaimer, the term of this patent is extended or adjusted under 35 U.S.C. 154(b) by 561 days.

(21) Appl. No.: 16/302,728

(22) PCT Filed: May 19, 2016

(86) PCT No.: PCT/JP2016/064825
§ 371 (c)(1),
(2) Date: Nov. 19, 2018

(87) PCT Pub. No.: WO2017/199387
PCT Pub. Date: Nov. 23, 2017

(65) Prior Publication Data
US 2019/0300829 A1      Oct. 3, 2019

(51) Int. Cl.
*C12M 3/00*      (2006.01)
*C12M 1/00*      (2006.01)
(Continued)

(52) U.S. Cl.
CPC .............. *C12M 21/08* (2013.01); *C12M 3/00* (2013.01); *C12M 29/04* (2013.01); *C12M 33/14* (2013.01); *C12N 5/0062* (2013.01)

(58) Field of Classification Search
None
See application file for complete search history.

(56) References Cited

U.S. PATENT DOCUMENTS

| 3,883,393 A | * | 5/1975 | Knazek | C12M 25/10 435/400 |
| 4,206,015 A | * | 6/1980 | Knazek | C12M 23/16 435/2 |

(Continued)

FOREIGN PATENT DOCUMENTS

| CN | 101007999 A | 1/2006 |
| CN | 101486967 A | 7/2009 |

(Continued)

OTHER PUBLICATIONS

Korean Office Action issued in corresponding Korean Patent Application No. 10-2018-7036842 dated May 21, 2020.

(Continued)

*Primary Examiner* — William H. Beisner
(74) *Attorney, Agent, or Firm* — Finch & Maloney PLLC

(57) ABSTRACT

A culture device and a culture method by which a substance to be cultured can be three-dimensionally cultured, and the substance thus cultured can be removed as an integrated product with multiple tubes; and a cultured organ produced by the culture method. The culture device comprises a sealed container (2) which contains the substance to be cultured (A) and is disassembled after the culture is completed; multiple ducts (3, 4, 5) arranged in the sealed container (2) and having a plurality of micropores formed on the outer peripheral surface; a culture medium-feeding device (6, 7) for feeding/circulating the culture medium (B) to at least one duct (3 or 5); an excretory device (8) connected to at least one duct (4) for excreting the waste product (C)permeating into the duct (4) through the micropores of the duct (4) from the substance to be cultured to the outside of the sealed container.

10 Claims, 5 Drawing Sheets

(51) Int. Cl.
*C12M 1/26* (2006.01)
*C12N 5/00* (2006.01)

(56) References Cited

U.S. PATENT DOCUMENTS

| | | | |
|---|---|---|---|
| 4,537,860 A | | 8/1985 | Tolbert et al. |
| 4,720,462 A | | 1/1988 | Rosenson |
| 4,948,736 A | * | 8/1990 | Kobayashi ............ C12M 25/10 210/275 |
| 5,043,260 A | * | 8/1991 | Jauregui ................ C12M 25/10 604/6.09 |
| 5,534,025 A | | 7/1996 | Moussy |
| 6,284,451 B1 | | 9/2001 | Funatsu et al. |
| 6,921,662 B2 | * | 7/2005 | Takagi .................. C12M 21/08 435/297.2 |
| 7,163,821 B2 | | 1/2007 | Uemura et al. |
| 8,846,307 B2 | | 9/2014 | Neumann |
| 9,127,242 B2 | | 9/2015 | Guertin et al. |
| 2003/0041800 A1 | | 3/2003 | Uemura et al. |
| 2004/0203147 A1 | | 10/2004 | Triffitt et al. |
| 2007/0224677 A1 | | 9/2007 | Neumann |
| 2011/0124078 A1 | * | 5/2011 | Edwards ................ C12M 29/16 435/174 |
| 2014/0087454 A1 | | 3/2014 | Li et al. |

FOREIGN PATENT DOCUMENTS

| | | | |
|---|---|---|---|
| CN | 202078585 U | * | 12/2011 |
| CN | 103080296 A | | 5/2013 |
| CN | 104611225 A | | 5/2015 |
| CN | 204779609 A | | 11/2015 |
| EP | 0363262 A1 | | 4/1990 |
| EP | 1078982 A2 | | 2/2001 |
| JP | 63-196286 A | | 8/1988 |
| JP | H11504216 | | 4/1999 |
| JP | 2001-128660 A | | 5/2001 |
| JP | 2002-315566 A | | 10/2002 |
| JP | 2003-70458 A | | 3/2003 |
| JP | 2004-201594 A | | 7/2004 |
| JP | 4059301 | | 12/2007 |
| JP | 2008-92935 A | | 4/2008 |
| JP | 2009-000012 A | | 1/2009 |
| JP | 2009-531067 A | | 9/2009 |
| JP | 2015062392 A | | 4/2015 |
| KR | 20120014137 A | | 2/2012 |
| WO | 9634090 A1 | | 10/1996 |
| WO | 2007/049576 A1 | | 5/2007 |
| WO | 2007112192 A2 | | 10/2007 |
| WO | 2010115185 A1 | | 10/2010 |
| WO | 2012016711 A1 | | 2/2012 |
| WO | 2015084168 A1 | | 6/2015 |

OTHER PUBLICATIONS

Neumann et al. "Tissue engineering of perfused microvessels", Microvascular Research, Academic Press, US, vol. 66, No. 1, Jul. 1, 2003, pp. 59-67, XP002595432.
European Search Report issued in corresponding European Patent Application No. 16902406.4 dated Dec. 16, 2019.
Australian Examination Report issued in corresponding Australian Patent Application No. 2016406837 dated Nov. 29, 2019.
Written Opinion filed in corresponding PCT Application No. PCT/JP2016/064825 dated Aug. 9, 2016.
International Search Report filed in corresponding PCT Application No. PCT/JP2016/064825 dated Aug. 9, 2016.
Chinese Office Action Corresponding to 202105280288950 dated Jun. 2, 2021.

* cited by examiner

CULTURE DEVICE, CULTURE METHOD AND CULTURED ORGAN PRODUCED BY THE CULTURE METHOD

TECHNICAL FIELD

The present invention relates to a culture device and a culture method for culturing three-dimensionally substance to be cultured such as tissue, cell, etc., and also to a cultured organ produced by the culture method.

BACKGROUND ART

In many of the conventional culture device for culturing three-dimensionally the substance to be cultured, the culture is carried out by forming the substance to be cultured in the form of cylinder (see, e.g., Patent Document 1) or holding the substance to be cultured on a cylindrical scaffold (see, e.g., Patent Document 2 or 3), then setting them into a culture chamber, and distributing the culture medium in the outside and inside of the substance to be cultured formed in the form of cylinder.

CITATION LIST

Patent Literature

Patent Literature 1: Japanese Patent Laid-open No. 2002-315566
Patent Literature 2: Japanese Patent No. 4059301
Patent Literature 3: Japanese Patent Laid-open No. 2008-92935

SUMMARY OF INVENTION

Technical Problem

Since, in the organism, the blood vessel and lymphatic vessel extend in the form of complicatedly branching or reticulating within tissue, it is difficult to reproduce three-dimensionally the tissue.

Also, a prolonged culture is required to culture and produce the tissue having function as organ. The culturing cell produces waste product on culturing. The waste product includes cytotoxic materials. For that reason, there are excretory ducts for exhausting the waste product and mucus (such as bile duct, pancreatic duct, conduit, etc.) in the organism. However, the conventional culture device is not provided with the excretory duct and the prolonged culture is not conducted in the convention culture device.

Therefore, when the conventional culture device is used, the three-dimensional culture is difficult and the cultured cell product having the form of several sheet layers is only produced. Currently, it is not possible to let the cultured materials to have the function as organ.

Hepatic artery and bile duct extend parallel in the organism, but the blood flow is opposite to the flow direction of bile. Because of the concentration gradient and difference of liver function in addition to the above-mentioned opposite flow direction, the waste product such as bile can effectively be excreted to bile duct.

In view of the above-mentioned problem of the conventional art, the present invention was made. It is an object of the present invention to provide a culture device and a culture method, by which it is possible to culture three-dimensionally the substance to be cultured by arranging multiple ducts, each of which has micropores formed on the outer peripheral surface, in a sealed container for containing the substance to be cultured and by feeding or circulating the culture medium to any of the multiple ducts and exhausting the waste product of the substance to be cultured through other ducts and it is also possible to implant into the organism the three-dimensionally cultured product as an integrated product with the multiple ducts after taking out it from the sealed container or it is possible to leave the three-dimensionally cultured product together with the sealed container within the organism. It is also an object of the present invention to provide the cultured organ produced by the culture method.

Solution to Problem

According to the present invention, the problem can be solved as follows:

(1) The culture device comprises a sealed container for containing substance to be cultured, said sealed container having a sealable input port for charging the substance to be cultured; multiple ducts arranged in the sealed container, each of ducts having a plurality of micropores formed on the outer peripheral surface; a culture medium-feeding device connected to at least one of the multiple ducts, said culture medium-feeding device feeding or circulating the culture medium to the at least one duct, so that the duct forms a culture medium-feeding duct; and an excretory device connected to at least one duct other than the culture medium-feeding duct among the multiple ducts, said excretory device exhausting the waste product permeating into the duct from the substance to be cultured through the micropores of the duct to the outside of the sealed container, so that the duct forms an excretory duct.

Because of the constitution, it is possible to feed the culture medium into the sealed container by the culture medium-feeding device and to exhaust the waste product of the substance to be cultured to the outside of the sealed container through the excretory duct and the excretory device, while holding the substance to be cultured within the sealed container, whereby it is possible to culture three-dimensionally the substance to be cultured for a prolonged period in the sealed container under the condition approximated to the organism of animal.

When the layout is variously modified by, for example, adopting one excretory duct and multiple culture medium-feeding ducts, it is possible to culture three-dimensionally the substance to be cultured, while reproducing the complex structure approximated to the various organs in the organism in the points such as complicated extending blood vessel and flow of blood or bile.

(2) In the above-mentioned item (1), the sealed container is of disassembly type.

Because of the constitution, it is possible to take out the cultured product of the substance to be cultured and the ducts as an integrated product by disassembling the sealed container after the culture is completed. The resultant cultured product can be implanted into the organism as a part of the tissue of animal just as it is.

At that time, the culture medium-feeding duct can serve as blood vessel. Accordingly, the cultured product after the implantation can maintain the function similar to the various organs of animal such as liver, pancreas, etc. by inosculating the culture medium-feeding duct to blood vessel and inosculating the excretory duct to gastrointestinal tract, bile duct, or the like.

(3) In the above-mentioned item (1), the sealed container is of capsule type.

Because of the constitution, it is possible to culture three-dimensionally the cell within the sealed container under the condition that the sealed container of capsule type is embedded in the organism.

(4) In any one of the above-mentioned items (1) to (3), any of the ducts within the sealed container is at least partially formed by semipermeable membrane.

Because of the constitution, the required ingredients can permeate from the culture medium circulating in the duct through the semipermeable membrane, said permeated ingredients being fed to the substance to be cultured, while the waste product of the substance to be cultured can be extracted into the duct through the semipermeable membrane.

(5) In any one of the above-mentioned items (1) to (3), any of the ducts within the sealed container is at least partially formed by unglazed cylindrical body.

Because of the constitution, it is possible to prepare cheaply the duct having the micropores.

(6) In any one of the above-mentioned items (1) to (5), the culture medium-feeding device is provided with a culture medium circulation circuit for circulating the culture medium to the culture medium-feeding duct, said culture medium circulation circuit being connected to both ends of the culture medium-feeding duct; a pump for circulating the culture medium, said pump being arranged in the culture medium circulation circuit; and a control box for controlling the circulating culture medium, said control box being arranged in the culture medium circulation circuit.

Because of the constitution, it is possible to simplify the structure of the culture medium-feeding device, while the culture medium is continuously and smoothly circulated to the culture medium-feeding duct.

(7) In any one of the above-mentioned items (1) to (6), the sealed container is at least partially formed by clear material.

Because of the constitution, it is possible to visually monitor the culture situation of the substance to be cultured from the outside so that it is possible to understand easily the stage of progress of culture.

(8) A culture method using the culture device according to the above-mentioned item (1) or (2) or to any one of items (4) to (7) referring to the item (2) comprises steps of culturing three-dimensionally the substance to be cultured in the sealed container by feeding the culture medium to the sealed container via the culture medium-feeding duct by the culture medium-feeding device and by exhausting the waste product of the substance to be cultured to the outside of the sealed container via the excretory duct and the excretory device, while holding the substance to be cultured in the sealed container; and taking out the cultured product of the substance to be cultured as an integrated product with the ducts from the sealed container by disassembling the sealed container after the culture is completed.

According to the culture method, it is possible to culture three-dimensionally the substance to be cultured for a prolonged period in the sealed container in the condition approximated to the organism of animal.

The integrated product of the substance to be cultured with the ducts, which is taken out by disassembling the sealed container after the culture is completed, can be implanted into the organism as a part of the tissue of animal just as it is.

(9) A culture method using the culture device according to the above-mentioned item (1) or (3) or to any one of items (4) to (7) referring to the item (3) comprises steps of embedding the sealed container containing the substance to be cultured in the organism and arranging the culture medium-feeding device and the excretory device in the outside of the organism; and culturing three-dimensionally the substance to be cultured in the sealed container, while the culture medium is fed to the sealed container through the culture medium-feeding duct by the culture medium-feeding device and the waste product of the substance to be cultured is exhausted to the outside of the sealed container through the excretory duct and the excretory device, while holding the substance to be cultured in the sealed container.

According to the culture method, it is possible to culture three-dimensionally the substance to be cultured for the prolonged period in the organism of animal. Accordingly, it is not necessary to create the same environment as the organism with difficulty. It is possible to culture effectively the substance to be cultured in the sealed container under the optimal environment.

Also, it is possible to abbreviating or simplifying the implantation operation by re-connecting the culture medium-feeding duct and the excretory duct to the blood vessel and bile duct, or the like, respectively, after the culture is completed or by leaving the sealed container in the organism, or by making the sealed container from a material which be able to melt in the organism after passing definite period of time.

(10) The cultured organ is made of an integrated product of the substance to be cultured with ducts.

According to the resultant cultured organ, it is possible to implant the integrated product of the substance to be cultured with the ducts, which is taken out from the sealed container, into the organism of animal as the cultured organ just as it is, or it is possible to leave the integrated product in the organism of animal.

At that time, the culture medium-feeding duct can serve as blood vessel. Accordingly, the integrated product after the implantation can maintain the function similar to the various organs of animal such as liver, pancreas, etc. by inosculating the culture medium-feeding duct to blood vessel and inosculating the excretory duct to gastrointestinal tract, bile duct, or the like.

Advantageous Effects of Invention

According to the present invention, the culture device and the culture method are provided, by which it is possible to culture three-dimensionally the substance to be cultured by arranging multiple ducts each of which has a plurality of micropores formed on the outer peripheral surface in a sealed container containing the substance to be cultured and by feeding or circulating the culture medium to any of the ducts and exhausting the waste product of the substance to be cultured through other ducts, so that it is possible to implant the three-dimensionally cultured product as an integrated product with the multiple ducts into the organism after taking out it form the sealed container, or it is also possible to leave the three-dimensionally cultured product as the integrated product with the sealed container in the organism. Also, the cultured organ produced by the culture method is provided.

DESCRIPTION OF EMBODIMENTS

Figure 1:
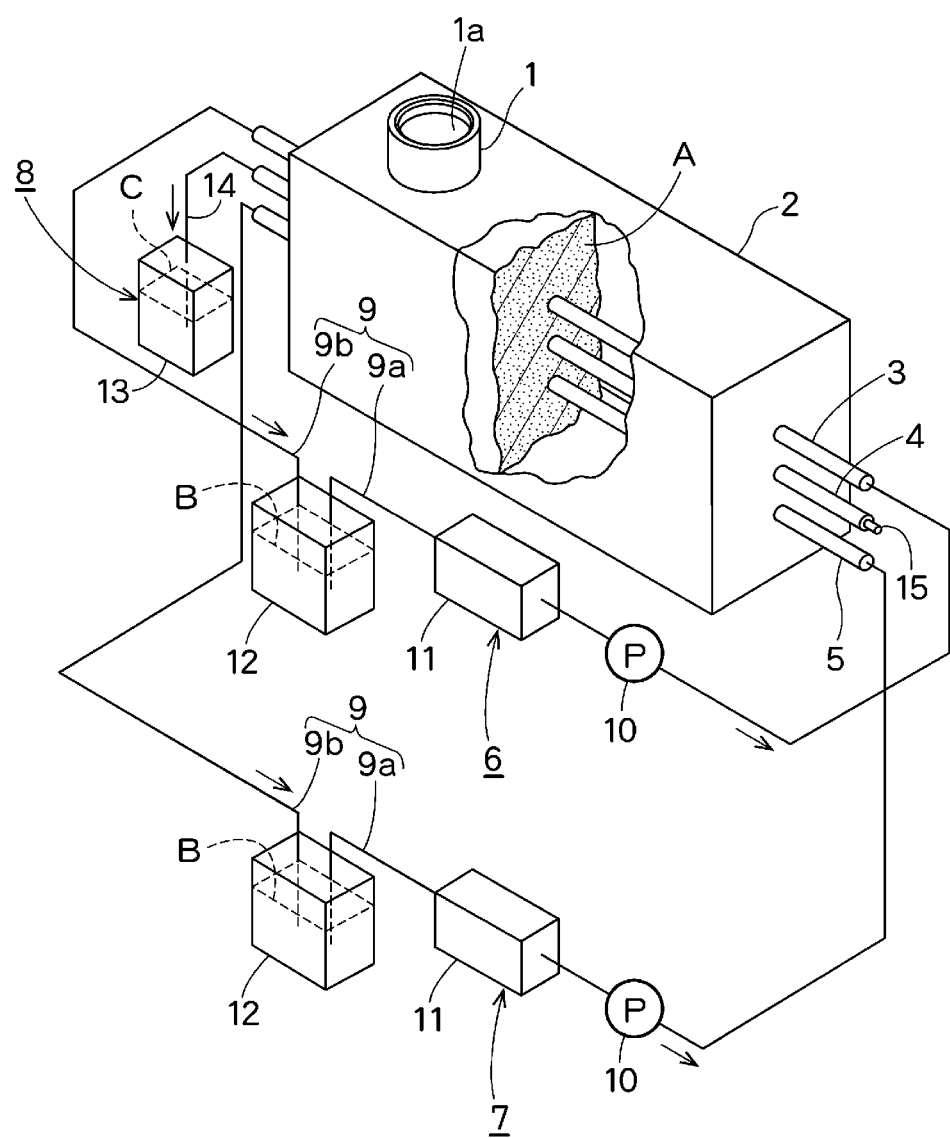
FIG. 1 is a partially broken perspective view showing schematically the first embodiment of the culture device of the present invention.

Now, the first embodiment of the culture device of the present invention is explained with referring the FIG. 1.

The culture device comprises a sealed container 2 having a sealable input port 1 for charging the substance to be cultured A (multiple input ports may be used), said sealed container being able to contain the substance to be cultured A and to be disassembled after the culture; multiple ducts 3, 4, 5 arranged in the sealed container 2, each of ducts having a plurality of micropores (not shown) formed on the outer peripheral surface; culture medium-feeding devices 6, 7 connected to at least one of the ducts 3, 4, 5, in this embodiment, two ducts 3, 5, respectively, the respective culture medium-feeding devices feeding or circulating the culture medium B to the duct 3, 5, so that the ducts form two culture medium-feeding ducts; and an excretory device 8 connected to at least one duct 4 other than the culture medium-feeding ducts 3, 5 among the ducts 3, 4, 5, said excretory device exhausting the waste product permeating into the duct 4 from the substance to be cultured A through the micropores of the duct to the outside of the sealed container 2, so that the duct 4 forms an excretory duct.

The input port 1 of the sealed container 2 can be sealed by a sealable lid 1a after charging the substance to be cultured A to the sealed container 2. Alternatively, the sealable lid 1a may be made of an elastic material such as rubber, etc. and the substance to be cultured A such as cell, etc. may be charged into the sealed container 2 via an injection needle, etc. (not shown) stuck into the sealable lid.

The sealed container 2 is a rectangular parallelepiped box made of clear acrylic plate, or glass plate, etc. The sealed container may be in the form of vertical or horizontal type cylinder, or other shapes.

It is possible to form only a part of the sealed container 2 by a clear material and to form the remaining by an opaque material.

According to this embodiment, the sealed container 2 is made of acrylic plate and after the culture it can be disassembled by cutting it at an optional place with a cutter, etc.

The sealed container 2 may be formed by using multiple divided bodies (not shown) and by inserting a packing into between the divided bodies and connecting them with bolt and nut. After the culture, the divided bodies may be disassembled by unlocking the bolt and nut or removing the connecting portion.

The conditions of duct 3, 4, 5 such as number, length, outer diameter, inner diameter, quality of material, diameter of the micropores, etc. are determined in accordance with the culture condition.

For example, the duct 3, 4, 5 is selected from cylindrical body made of semi-permeable membrane or unglazed earthenware, blood vessel prosthesis, etc. The duct 3, 4, 5 may be formed by the cylindrical body made of semi-permeable membrane or unglazed earthenware only at its portion present within the sealed container 2 and by a cylindrical body made of synthetic resin at its other portion.

The duct 3, 4, 5 has preferably the outer diameter of several mm to tens mm and the mean diameter of the micropores of 100 to 10,000 Å.

The ducts 3, 4, 5 may differ from each other in quality of material, size, and the mean diameter of the micropores, etc. in accordance with a use of duct.

It is desirable that the duct 3, 4, 5 has flexibility, but that is not essential.

According to this embodiment, the respective ducts 3, 4, 5 penetrate in horizontal direction through the sealed container 2 and their both ends project from both sides of the sealed container 2.

In order to prevent the culture medium B, etc. mentioned below from leaking from the respective ducts 3, 4, 5 situated at the outside of the sealed container, the area wherein the micropores are formed in the respective ducts 3, 4, 5 is limited, or the micropores are formed throughout the respective ducts 3, 4, 5, following by coating airtightly or liquid-tightly the periphery of the respective ducts situated at the outside of the sealed container 2 or by fitting externally a flexible tube (not shown) to the respective ducts situated in the outside of the sealed container 2.

The respective culture medium-feeding devices 6, 7 comprise a culture medium circulation circuit 9 for circulating the culture medium B to the culture medium-feeding duct 3, 5, said culture medium circulation circuit 9 being connected to both ends of the culture medium-feeding duct 3, 5; a pump 10 for circulating the culture medium B, said pump 10 being arranged in the culture medium circulation circuit 9; and a control box 11 for controlling the temperature, pressure, oxygen concentration, ingredient distribution, etc. of the circulating culture medium B, said control box being arranged in the culture medium-feeding circulation circuit 9.

The respective culture medium-feeding devices 6, 7 comprise a liquid reservoir 12 in the culture medium circulation circuit 9, the culture medium circulation circuit 9 comprising a liquid-feeding duct 9a leading from the liquid reservoir 12 to one end of the respective ducts 3, 5 via the control box 11 and the pump 10; and a liquid-exhausting duct 9b leading from the other end of the respective ducts 3, 5 to the liquid reservoir 12.

An excretory device 8 comprises a waste product-containing vessel 13 arranged in the outside of the sealed container 2; and a sending duct 14 for sending the waste product C accumulating within the excretory duct 4 to the waste product-containing vessel 13.

The other end of the excretory duct 4 is closed by a plug 15.

Now, an embodiment of the culture method of the present invention which is carried out by using the above-mentioned culture device is explained.

As being shown in FIG. 1, the input port 1 of the sealed container 2 is open and the substance to be cultured A is charged into the sealed container 2 and then the input port 1 is sealed by the sealable lid 1a.

The substance to be cultured A may be as follows:

(1) multiple cells dispersed in culture medium of liquid type or of gel type and floating therein;

(2) small aggregate of cells floating in culture medium of liquid type or of gel type.

After the substance to be cultured A is charged into the sealed container 2 and the input port 1 is sealed, the culture medium B is circulated into the culture medium-feeding ducts 3, 5 by the culture medium-feeding devices 6, 7.

Then, the essential ingredients contained in the culture medium B permeate to the side of the substance to be cultured A within the sealed container 2 through the micropores of the respective culture medium-feeding ducts 3, 5 so that the culture of the substance to be cultured A is prompted.

The culture medium B is selected from well-known preparations containing one or two or more of collagen, elastin, proteoglycan, fibrillin, fibronectin, laminin, chitin, chitosan, blood, etc.

The waste product C of the substance to be cultured A permeates into the excretory duct 4 through the micropores of the excretory duct 4 and is sent to the waste product-containing vessel 13 through the feeding duct 14 and is stored in the waste product-containing vessel 13.

Thus, the waste product C of the substance to be cultured A is exhausted to the outside of the sealed container 2 through the excretory duct 4 and feeding duct 14 and accordingly, the waste product C do not stay in the substance to be cultured A, whereby it is possible to carry out effectively the three-dimensional culture for a prolonged period.

According to the culture method, it is possible to culture three-dimensionally the substance to be cultured A for a prolonged period in the sealed container 2 under the conditions approximate to the complicated structure of various organs in the organism of animal.

It is possible to take out the cultured product of the substance to be cultured A and the ducts 3, 4, 5 as an integrated product by disassembling the sealed container 2 after the culture is completed. The resultant integrated product can be implanted into the organism as cultured organ just as it is.

At that time, the culture medium-feeding ducts 3, 5 can serve as blood vessel. Accordingly, the integrated product after the implantation can maintain the function similar to the various organs of animal such as liver, pancreas, etc. by inosculating the culture medium-feeding ducts 3, 5 to blood vessel and inosculating the excretory duct 4 to gastrointestinal tract, bile duct, or the like.

FIGS. 2 to 6 show the second embodiment of the culture device of the present invention.

In the second embodiment, the sealed container 20 is in the form of capsule consisting of hemispheres 20b, 20b connected to the both ends of cylindrical part 20a, said cylindrical part being provided at an optional position with the input port 21 for charging the substance to be cultured A into the sealed container 20.

The sealable lid 22 is arranged detachably to the input port 21.

It is preferable that when the sealable lid 22 is mounted suitably on the input port 21, the surface of the sealable lid 22 matches with the outer surface of the cylindrical part 20a of the sealed container 20.

The sealed container 20 and sealable lid 22 are preferably formed by synthetic resin having flexibility, biomaterial having compatibility to the organism such as collagen fiber, etc., or material able to melt after the period longer than the predetermined culture period lapse on being embedded in the organism. There are exemplified as actual material nylon, reinforced glass, reinforced plastics, silicone rubber, silicone prosthesis, etc.

Figure 3:
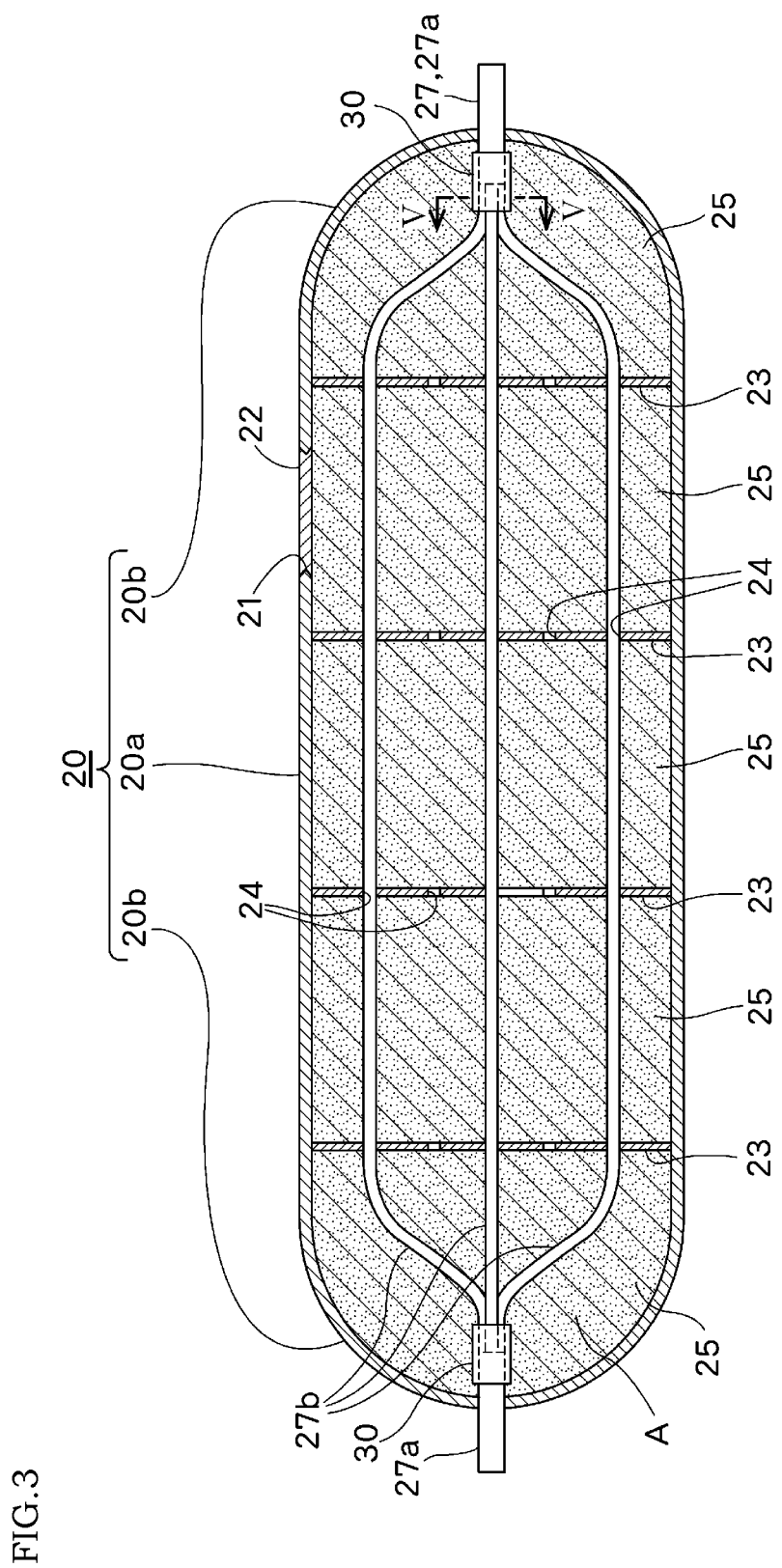
FIG. 3 is a longitudinal sectional view with respect to the line III-III in FIG. 2.
Figure 6:
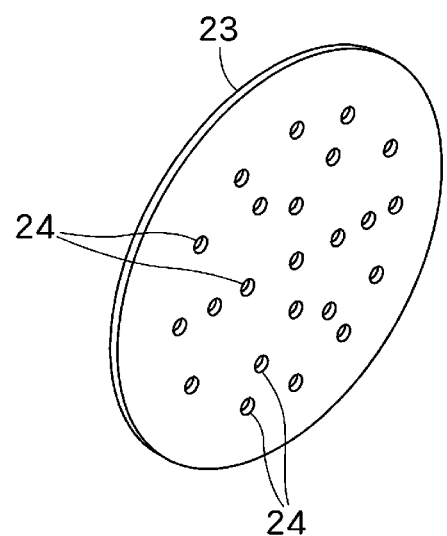
FIG. 6 is a perspective view showing an embodiment of partition wall used in the second embodiment.

As being shown in FIG. 3 and FIG. 6, multiple partition walls 23 made of the same biomaterial as above-mentioned biomaterial are arranged within the sealed container 20 at the suitable intervals in the horizontal direction.

The respective partition walls 23 have multiple small holes 24 arranged in the predetermined configuration or random configuration.

The inner space of the sealed container 20 is divided into multiple cells 25 by the respective partition walls 23.

The multiple small holes 24 formed in the respective partition walls 23 allow the substance to be cultured A and the culture medium B to migrate between respective cells 25, 25 and have the function of holding the below-mentioned small diameter ducts 26b-29b inserted into any of small holes 24 at the predetermined position in the sealed container 20. The shape and size of the multiple small holes 24 formed in the respective partition walls 23 are suitably modifiable. It is possible to block the migration of substance to be cultured A and culture medium B between the respective cells 25, 25 by the partition walls 23.

The sealed container 20 has four ducts 26-29 arranged in the manner that they penetrate through the sealed container in longitudinal direction.

Figure 5:
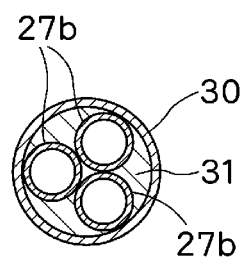
FIG. 5 is an enlarged longitudinal sectional view with respect to the line V-V in FIG. 3.

In the second embodiment, as being shown in FIG. 3, the respective ducts 26-29 consist of multiple large diameter ducts 26a-29a penetrating through the hemisphere parts 20b at the both ends of the sealed container 20, while maintaining airtightness and liquid-tightness, and multiple small diameter ducts 26b-29b which are mutually bundled at their both ends in the sealed container 20 and are, as being shown in FIG. 3 and FIG. 5, connected to the large diameter ducts 26a-29a by a connecting pipe 30 made of elastic material such as rubber, etc.

The peripheral surface of respective small diameter ducts 26b-29b is provided with a plurality of micropores (not shown) similar to the micropores formed in the ducts 3, 4, 5 of the first embodiment.

As being shown in FIG. 5, it is preferable to keep the airtightness and liquid-tightness in the connecting part by providing the sealing material 31 into the space formed by the bundling part in which the ends of multiple small diameter ducts 26b-29b are mutually bundled and the space formed by the connecting pipe 30 and the bundling part.

The respective small diameter ducts 26b-29b are held at the predetermined position by penetrating through any of the small holes 24 of the respective partition walls 23, so that they do not get entangled.

Omitting to show in the figure, both ends of three ducts among the four ducts 26-29, for example, ducts 26, 28, 29 are connected to a culture medium-feeding device (not shown) similar to the culture medium-feeding device 6 or 7 connected to the duct 3 or 5 in the first embodiment. One end of remaining duct 27 is connected to an excretory device (not shown) similar to the excretory device 8 connected to the duct 4 in the first embodiment and another end of the duct 27 is closed by a plug (not shown) pressed into the end, which is similar to the plug 15 in the first embodiment.

Accordingly, in this embodiment, the ducts 26, 28 and 29 serve as a culture medium-feeding duct and the duct 27 serves as an excretory duct.

In order to facilitate the engraftment of cell within the sealed container 20 and to prevent the duct 26, 27, 28, 29 from clogging by blood cake, etc., it is desirable to enclose fiber for engraftment in the sealed container 20, or to implant fine fiber on inner surface of the sealed container 20 or surface of the partition wall 23, etc., or to cover the surfaces with a material capable of easy engraftment of cell or to cover the inner surface of the duct 26, 27, 28, 29 with a material which renders engraftment of cell difficult.

Now, an embodiment of the culture method of the present invention, which is carried out by using the second embodiment of the above-mentioned culture device is explained.

Figure 2:
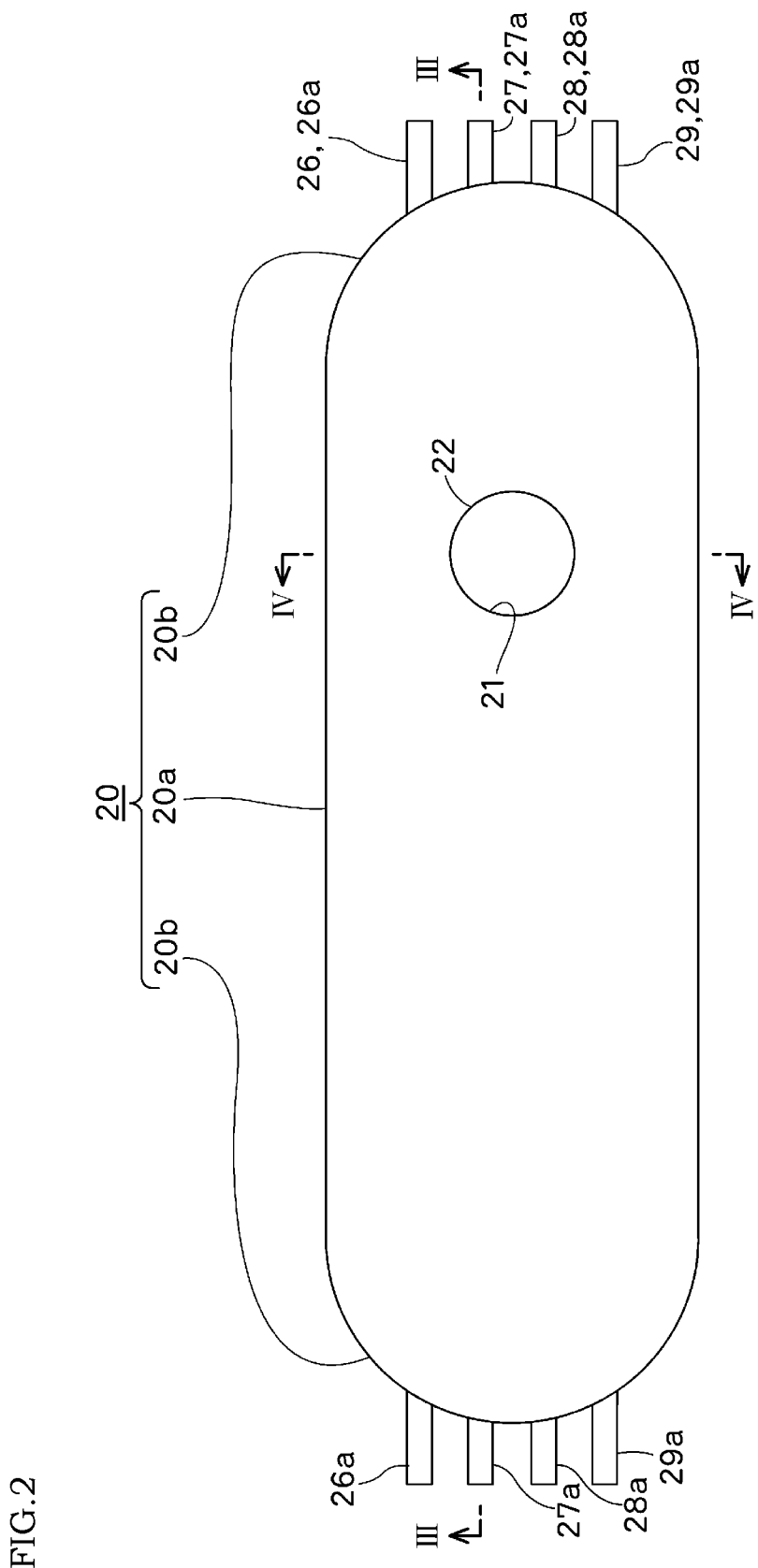
FIG. 2 is a plan view showing a part of the second embodiment of the culture device of the present invention.
Figure 4:
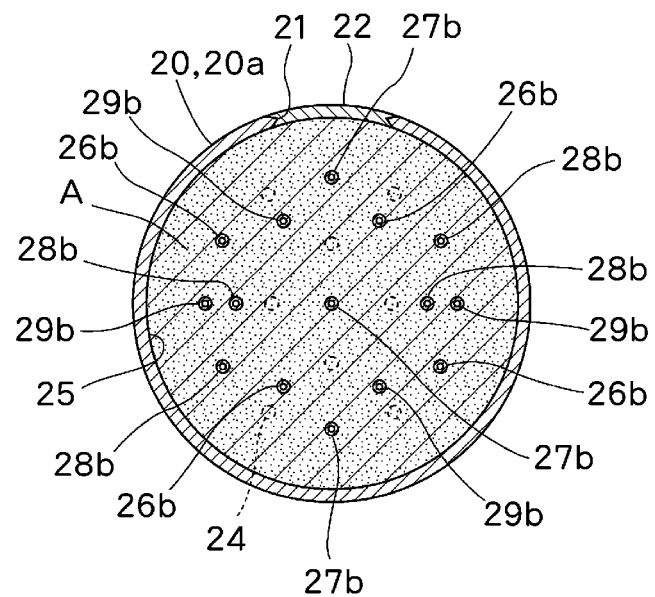
FIG. 4 is a longitudinal sectional view with respect to the line IV-IV in FIG. 2.

In the state shown in FIGS. 2-4, the sealable lid 22 is removed from the input port 21 of the sealed container 20 to open the input port 21. The substance to be cultured A is charged into the sealed container 20 therefrom and the sealable lid 22 is mounted on the input port 21 to seal the input port 21.

Then, both ends of the respective ducts 26, 28, 29 are connected to the culture medium-feeding device, and one end of the duct 27 is connected to the excretory device and the plug is compressed into another end of the duct 27 to close the end.

The sealed container 20 and the ducts 26-29 connected to the sealed container are embedded in the organism of animal (not shown) as it is in this state.

Then, the pump in the respective culture medium-feeding devices (refer to the pump 10 in FIG. 1) is actuated to circulate the culture medium B similar to the above-mentioned culture medium to the ducts 26, 28, 29.

The culture medium B circulating in the respective ducts 26, 28, 29 is same as each other or may be different from each other.

In this way, the waste product C of the substance to be cultured A, which permeates into the small diameter duct 27b through the micropores of the small diameter duct 27b of the excretory duct 27, is exhausted to the outside of the sealed container 20 via the large diameter duct 27a, while circulating the culture medium B to the respective culture medium-feeding ducts 26, 28, 29. As a result, as with the first embodiment, it is possible to culture three-dimensionally and effectively the substance to be cultured A in the sealed container 20 for a prolonged period, while the waste product C do not stay in the substance to be cultured A.

According to this culture method, the sealed container 20 is embedded in the organism and the three-dimensional culture of the substance to be cultured A is conducted therein and accordingly, it is possible to maintain the same conditions such as temperature, etc. as the organism.

After the culture is completed, when, for example, the ducts 26, 28, 29, and 27 are inosculated to a hepatic artery, a portal vein, a bile duct, and a hepatic vain (in the case that the substance to be cultured A is liver cell) of the organism, respectively and the sealed container 20 is left in the organism, it is possible to use the cultured cell as a part of the organism just as it is.

In this case, when the sealed container 20 is made of a material capable of melting in the organism after passing definite period of time, it is not required to take out the sealed container 20 from the organism.

The number of the ducts 26-29, number and diameter of the small diameter ducts 26b-29b with respect to the large diameter ducts 26a-29a in the respective ducts 26-29, how to branch, arrangement thereof, etc. may be varied in accordance with type of the substance to be cultured A, condition of recipient, etc.

The present invention is not limited only to the above-mentioned embodiments, and can be carried out in accordance with the following many modified embodiments without departing the scope and spirit of the Claims.

(1) One end of the culture medium-feeding duct 3 or 5 is closed and the culture medium B is fed to the sealed container via another end.

(2) Either of the ducts 3 and 5 is omitted and accordingly either of the culture medium-feeding devices 6 and 7 is omitted.

(3) Either of the ducts 3 and 5 is used as lymphatic vessel.

(4) The ducts 3, 4 and 5 are used as blood duct, excretory duct, and lymphatic vessel, respectively.

(5) The substance to be cultured A is three-dimensionally cultured, while reproducing the complicated structure similar to the structure of organs in the organism in the points of complicated extending of blood vessels, flow of blood and bile, by using one duct as the excretory duct 4 and multiple ducts as the culture medium-feeding duct 3, 5 and by modifying the layout of ducts.

(6) The respective ducts 3, 4, 5 are arranged in the different direction in the sealed container 20.

REFERENCE SIGNS LIST

A substance to be cultured
B culture medium
C waste product
1 input port
1a salable lid
2 sealed container
3 duct (culture medium-feeding duct)
4 duct (excretory duct)
5 duct (culture medium-feeding duct)
6, 7 culture medium-feeding device
8 excretory device
9 culture medium circulation circuit
9a liquid-feeding duct
9b liquid-excreting duct
10 pump
11 control box
12 liquid reservoir
13 waste product containing vessel
14 feeding duct
15 plug
20 sealed container
20a cylindrical part
20b hemisphere part
21 input port
22 salable lid
23 partition wall
24 small pore
25 cell
26, 28, 29 duct (culture medium-feeding duct)
27 duct (excretory duct)
26a-29a large diameter duct
26b-29b small diameter duct
30 connecting duct
31 sealing material

The invention claimed is:

1. A culture device for producing a cultured organ comprising an integrated product of a substance to be cultured and multiple ducts, the culture device comprising:
 a sealed container for containing the substance to be cultured, and said sealed container having a sealable input port for charging the substance to be cultured;
 the multiple ducts arranged in the sealed container, and each of said ducts having a plurality of micropores formed on an outer peripheral surface;
 a culture medium-feeding device connected to at least one of the multiple ducts, and said culture medium-feeding device feeding or circulating the culture medium to the at least one of the multiple ducts so that the at least one of the multiple ducts forms a culture medium-feeding duct, the culture medium-feeding device comprising a culture medium circulation circuit for circulating the culture medium to the culture medium-feeding duct, which is connected to both ends of the culture medium-feeding duct, a pump for circulating the culture medium, which is arranged in the culture medium circulation circuit, and a control box for controlling the circulating culture medium, which is arranged in the culture medium circulation circuit; and an excretory device connected to at least one duct other than the culture medium-feeding duct among the multiple ducts, said excretory device exhausting waste product permeating into the at least one duct other than the culture medium-feeding duct from the substance to be cultured through the micropores of the at least one duct other than the culture medium-feeding duct to the outside of the sealed container so that the at least one duct other than the culture medium-feeding duct forms an excretory duct, the excretory device comprising a waste product-containing vessel arranged in the outside of the sealed container, and a sending duct for sending the waste product accumulating within the excretory duct to the waste product-containing vessel, wherein the culture device further comprises at least one partition wall which is arranged in the sealed container so as to divide an inner space of the sealed container into multiple cells and is formed with multiple small holes, the multiple ducts being inserted into some of the multiple small holes in said at least one partition wall so as to be held, and remaining multiple small holes in said at least one partition wall allowing both of the substance to be cultured and the culture medium to migrate between respective cells, wherein a plurality of the culture medium-feeding ducts is provided such that each of the culture medium-feeding ducts is branched into a plurality of small diameter ducts in the sealed container, each of the small diameter ducts having the micropores formed on the outer peripheral surface, and the small diameter ducts of each of the culture medium-feeding ducts are respectively inserted into the multiple small holes in said at least one partition wall, wherein the excretory duct is branched into a plurality of small diameter ducts in the sealed container, each of the small diameter ducts having the micropores formed on the outer peripheral surface, and the small diameter ducts of the excretory duct are respectively inserted into the multiple small holes in said at least one partition wall, wherein each of the culture medium-feeding ducts is provided with the culture medium-feeding device, and the culture medium circulating in each of the plurality of culture medium-feeding ducts is the same or are different from the culture medium circulating in another of the plurality of culture medium-feeding ducts, wherein the culture medium-feeding ducts are made to reproduce three-dimensionally a structure approximated to blood vessels or blood and lymphatic vessels of an organ in an organism, the organ being an implantation target by the cultured organ, by configuring the following: the number, mean diameter of the micropores, and quality of material of the culture medium-feeding ducts; the number, diameter, way of branching, and arrangement of the small diameter ducts of each of the culture medium-feeding ducts; and arrangement of the multiple small holes for the small diameter ducts of each of the culture medium-feeding ducts in said at least one partition wall, and wherein the excretory duct is made to reproduce three-dimensionally a structure approximated to an excretory duct of the organ that is the implantation target by the cultured organ, by configuring the following: the number, mean diameter of the micropores, and quality of material of the excretory duct of the culture device; the number, diameter, way of branching, and arrangement of the small diameter ducts of the excretory duct and arrangement of the multiple small holes for the small diameter ducts of the excretory duct in said at least one partition wall.

2. The culture device according to claim 1, wherein the sealed container is disassembled after culture by cutting at an optional place, or the sealed container is formed with multiple divided bodies so as to be disassembled after culture.

3. The culture device according to claim 1, wherein the sealed container is in a form of a capsule comprising a cylindrical part and a pair of hemispheres respectively connected to both ends of the cylindrical part.

4. The culture device according to claim 1, wherein at least one of the ducts within the sealed container is at least partially formed by semipermeable membrane.

5. The culture device according to claim 1, wherein at least one of the ducts within the sealed container is at least partially formed by unglazed cylindrical body.

6. The culture device according to claim 1, wherein the sealed container is at least partially formed by a clear material.

7. The culture device according to claim 1,
wherein the substance to be cultured is liver cells,
wherein the culture medium-feeding ducts are made to reproduce three-dimensionally a structure approximated to a hepatic artery, a portal vein, and a hepatic vein of a liver in the organism, the liver being the implantation target by the cultured organ, by configuring the following: the number, mean diameter of the micropores, and quality of material of the culture medium-feeding ducts; the number, diameter, way of branching, and arrangement of the small diameter ducts of each of the culture medium-feeding ducts; and arrangement of the multiple small holes for the small diameter ducts of each of the culture medium-feeding ducts in said at least one partition wall, and
wherein the excretory duct of the culture device is made to reproduce three-dimensionally a structure approximated to a bile duct of the liver that is the implantation target by the cultured organ, by configuring the following: the number, mean diameter of the micropores, and quality of material of the excretory duct of the culture device; the number, diameter, way of branching, and arrangement of the small diameter ducts of the excretory duct; and arrangement of the multiple small holes for the small diameter ducts of the excretory duct in said at least one partition wall.

8. The culture device according to claim 1, wherein
the culture medium-feeding ducts are made to reproduce three-dimensionally a structure approximated to blood vessels of a pancreas in the organism, the pancreas being the implantation target by the cultured organ, by configuring the following: the number, mean diameter of the micropores, and quality of material of the culture medium-feeding ducts; the number, diameter, way of branching, and arrangement of the small diameter ducts of each of the culture medium-feeding ducts; and arrangement of the multiple small holes for the small diameter ducts of each of the culture medium-feeding ducts in said at least one partition wall, and
wherein the excretory duct of the culture device is made to reproduce three-dimensionally a structure approximated to an excretory duct of the pancreas connecting the pancreas to a gastrointestinal tract, the pancreas being the implantation target by the cultured organ, by configuring the following: the number, mean diameter of the micropores, and quality of material of the excretory duct of the culture device; the number, diameter, way of branching, and arrangement of the small diameter ducts of the excretory duct; and arrangement of the multiple small holes for the small diameter ducts of the excretory duct in said at least one partition wall.

9. A culture method employing a culture device for producing a cultured organ comprising an integrated product of a substance to be cultured and multiple ducts, the culture device comprising:
   a sealed container for containing the substance to be cultured, and said sealed container having a sealable input port for charging the substance to be cultured;
   the multiple ducts arranged in the sealed container, and each of said ducts having a plurality of micropores formed on the outer peripheral surface;
   a culture medium-feeding device connected to at least one of the multiple ducts, and said culture medium-feeding device feeding or circulating the culture medium to the at least one of the multiple ducts so that the at least one of the multiple ducts forms a culture medium-feeding duct, the culture medium-feeding device comprising a culture medium circulation circuit for circulating the culture medium to the culture medium-feeding duct, which is connected to both ends of the culture medium-feeding duct, a pump for circulating the culture medium, which is arranged in the culture medium circulation circuit, and a control box for controlling the circulating culture medium, which is arranged in the culture medium circulation circuit; and
   an excretory device connected to at least one duct other than the culture medium-feeding duct among the multiple ducts, said excretory device exhausting waste product permeating into the at least one duct other than the culture medium-feeding duct from the substance to be cultured through the micropores of the at least one duct other than the culture medium-feeding duct to the outside of the sealed container so that the at least one duct other than the culture medium-feeding duct forms an excretory duct, the excretory device comprising a waste product-containing vessel arranged in the outside of the sealed container, and a sending duct for sending the waste product accumulating within the excretory duct to the waste product-containing vessel,
   wherein the culture device further comprises at least one partition wall which is arranged in the sealed container so as to divide an inner space of the sealed container into multiple cells and is formed with multiple small holes, the multiple ducts being inserted into some of the multiple small holes in said at least one partition wall so as to be held, and the remaining multiple small holes in said at least one partition wall allowing both of the substance to be cultured and the culture medium to migrate between respective cells,
   wherein a plurality of the culture medium-feeding ducts is provided such that each of the culture medium-feeding ducts is branched into a plurality of small diameter ducts in the sealed container, each of the small diameter ducts having the micropores formed on the outer peripheral surface, and the small diameter ducts of each of the culture medium-feeding ducts are respectively inserted into the multiple small holes in said at least one partition wall,
   wherein the excretory duct is branched into a plurality of small diameter ducts in the sealed container, each of the small diameter ducts having the micropores formed on the outer peripheral surface, and the small diameter ducts of the excretory duct are respectively inserted into the multiple small holes in said at least one partition wall,
   wherein each of the culture medium-feeding ducts is provided with the culture medium-feeding device, and the culture medium circulating in each of the plurality of culture medium-feeding ducts is the same or are different from the culture medium circulating in another of the plurality of culture medium-feeding ducts,
   wherein the culture medium-feeding ducts are made to reproduce three-dimensionally a structure approximated to blood vessels or blood and lymphatic vessels of an organ in an organism, the organ being an implantation target by the cultured organ, by configuring the following: the number, mean diameter of the micropores, and quality of material of the culture medium-feeding ducts; the number, diameter, way of branching, and arrangement of the small diameter ducts of each of the culture medium-feeding ducts; and arrangement of the multiple small holes for the small diameter ducts of each of the culture medium-feeding ducts in said at least one partition wall, and
   wherein the excretory duct is made to reproduce three-dimensionally a structure approximated to an excretory duct of the organ that is the implantation target by the cultured organ, by configuring the following: the number, mean diameter of the micropores, and quality of material of the excretory duct of the culture device; the number, diameter, way of branching, and arrangement of the small diameter ducts of the excretory duct and arrangement of the multiple small holes for the small diameter ducts of the excretory duct in said at least one partition wall, said culture method comprising:
   culturing three-dimensionally the substance to be cultured in the sealed container by feeding the culture medium to the sealed container via each of the culture medium-feeding ducts by a respective culture medium-feeding device and by exhausting the waste product of the substance to be cultured to the outside of the sealed container via the excretory duct and the excretory device, while holding the substance to be cultured in the sealed container; and
   after the culture is completed, taking out the cultured product of the substance to be cultured as an integrated product with the ducts from the sealed container by disassembling the sealed container.

10. A culture method utilizing a culture device for producing a cultured organ comprising an integrated product of a substance to be cultured and multiple ducts, the culture device comprising:
    a sealed container for containing the substance to be cultured, and said sealed container having a sealable input port for charging the substance to be cultured;
    the multiple ducts arranged in the sealed container, and each of said ducts having a plurality of micropores formed on the outer peripheral surface;
    a culture medium-feeding device connected to at least one of the multiple ducts, and said culture medium-feeding device feeding or circulating the culture medium to the at least one of the multiple ducts so that the at least one of the multiple ducts forms a culture medium-feeding duct, the culture medium-feeding device comprising a culture medium circulation circuit for circulating the culture medium to the culture medium-feeding duct, which is connected to both ends of the culture medium-feeding duct, a pump for circulating the culture medium, which is arranged in the culture medium circulation circuit, and a control box for controlling the circulating culture medium, which is arranged in the culture medium circulation circuit; and an excretory device connected to at least one duct other than the culture medium-feeding duct among the multiple ducts, said excretory device exhausting waste product permeating into the at least one duct other than the culture medium-feeding duct from the substance to be cultured through the micropores of the at least one duct other than the culture medium-feeding duct to the outside of the sealed container so that the at least one duct other than the culture medium-feeding duct forms an excretory duct, the excretory device comprising a waste product-containing vessel arranged in the outside of the sealed container, and a sending duct for sending the waste product accumulating within the excretory duct to the waste product-containing vessel, wherein the culture device further comprises at least one partition wall which is arranged in the sealed container so as to divide an inner space of the sealed container into multiple cells and is formed with multiple small holes, the multiple ducts being inserted into some of the multiple small holes in said at least one partition wall so as to be held, and the remaining multiple small holes in said at least one partition wall allowing both of the substance to be cultured and the culture medium to migrate between respective cells, wherein a plurality of the culture medium-feeding ducts is provided such that each of the culture medium-feeding ducts is branched into a plurality of small diameter ducts in the sealed container, each of the small diameter ducts having the micropores formed on the outer peripheral surface, and the small diameter ducts of each of the culture medium-feeding ducts are respectively inserted into the multiple small holes in said at least one partition wall, wherein the excretory duct is branched into a plurality of small diameter ducts in the sealed container, each of the small diameter ducts having the micropores formed on the outer peripheral surface, and the small diameter ducts of the excretory duct are respectively inserted into the multiple small holes in said at least one partition wall, wherein each of the culture medium-feeding ducts is provided with the culture medium-feeding device, and the culture medium circulating in each of the plurality of culture medium-feeding ducts is the same or are different from the culture medium circulating in another of the plurality of culture medium-feeding ducts, wherein the culture medium-feeding ducts are made to reproduce three-dimensionally a structure approximated to blood vessels or blood and lymphatic vessels of an organ in an organism, the organ being an implantation target by the cultured organ, by configuring the following: the number, mean diameter of the micropores, and quality of material of the culture medium-feeding ducts; the number, diameter, way of branching, and arrangement of the small diameter ducts of each of the culture medium-feeding ducts; and arrangement of the multiple small holes for the small diameter ducts of each of the culture medium-feeding ducts in said at least one partition wall, and wherein the excretory duct is made to reproduce three-dimensionally a structure approximated to an excretory duct of the organ that is the implantation target by the cultured organ, by configuring the following: the number, mean diameter of the micropores, and quality of material of the excretory duct of the culture device; the number, diameter, way of branching, and arrangement of the small diameter ducts of the excretory duct and arrangement of the multiple small holes for the small diameter ducts of the excretory duct in said at least one partition wall, said culture method comprising:

embedding the sealed container, containing the substance to be cultured, in the organism and arranging the culture medium-feeding device and the excretory device in the outside of the organism; and culturing three-dimensionally the substance to be cultured in the sealed container by feeding the culture medium to the sealed container via each of the culture medium-feeding ducts by a respective culture medium-feeding device and by exhausting the waste product of the substance to be cultured to the outside of the sealed container via the excretory duct and the excretory device, while holding the substance to be cultured in the sealed container.

* * * * *